United States Patent
Guy

(10) Patent No.: US 10,884,128 B2
(45) Date of Patent: Jan. 5, 2021

(54) SYSTEM AND METHOD OF UNDERGROUND WATER DETECTION

(71) Applicant: Utilis Israel Ltd., Rosh HaAyin (IL)

(72) Inventor: Lauren Guy, Beer-Sheva (IL)

(73) Assignee: Utilis Israel Ltd., Kfar-Saba (IL)

( * ) Notice: Subject to any disclaimer, the term of this patent is extended or adjusted under 35 U.S.C. 154(b) by 62 days.

(21) Appl. No.: 15/917,944

(22) Filed: Mar. 12, 2018

(65) Prior Publication Data

US 2018/0224550 A1    Aug. 9, 2018

Related U.S. Application Data

(63) Continuation-in-part of application No. 15/014,053, filed on Feb. 3, 2016, now Pat. No. 9,945,942, which
(Continued)

(51) Int. Cl.
*G01S 17/58*   (2006.01)
*G01S 13/88*   (2006.01)
(Continued)

(52) U.S. Cl.
CPC ............ *G01S 17/58* (2013.01); *G01M 3/183* (2013.01); *G01M 3/40* (2013.01); *G01N 22/00* (2013.01);
(Continued)

(58) Field of Classification Search
CPC ...... G01S 17/58; G01S 13/904; G01S 13/885; G01S 7/025; G01S 7/411; G01S 13/855;
(Continued)

(56) References Cited

U.S. PATENT DOCUMENTS

| 2,884,624 A | 4/1959 | En Dean |
| 3,623,111 A | 11/1971 | Provencher et al. |

(Continued)

FOREIGN PATENT DOCUMENTS

| CN | 102819047 | 12/2012 |
| CN | 103748318 | 4/2014 |

(Continued)

OTHER PUBLICATIONS

Komarov et al., "Permittivity and Measurements", p. 3693-3711.
(Continued)

*Primary Examiner* — Bryan Bui
(74) *Attorney, Agent, or Firm* — Pearl Cohen Zedek Latzer Baratz LLP

(57) ABSTRACT

Embodiments of the invention are directed to a method of determining underground liquid content (e.g., water, sewage, etc.). Embodiments may include: receiving, from a radiofrequency radiation sensor, a main scan of an area, the main scan may include reflections from the area at RF range, and receiving typical roughness values of one or more types of water sources. Embodiments may further include: filtering from the main scan undesired water source types according to their typical roughness values, identifying a desired type of water source in the filtered main scan and receiving from the RF radiation sensor a set of scans of the area, each scan of the area includes reflections in the RF range taken prior to the receiving of the main scan. Embodiments may include calculating the underground water content at locations in the area based on the identified first type of water source and the received set of scans.

18 Claims, 13 Drawing Sheets

Related U.S. Application Data is a continuation-in-part of application No. 14/666,648, filed on Mar. 24, 2015, now Pat. No. 9,285,475.

(51) Int. Cl.

| | | |
|---|---|---|
| *G01S 7/41* | (2006.01) | |
| *G01S 7/02* | (2006.01) | |
| *G01N 33/18* | (2006.01) | |
| *G01N 22/00* | (2006.01) | |
| *G01M 3/18* | (2006.01) | |
| *G01V 8/00* | (2006.01) | |
| *G01V 9/02* | (2006.01) | |
| *G01S 13/90* | (2006.01) | |
| *G01M 3/40* | (2006.01) | |
| *G01S 13/86* | (2006.01) | |
| *G01V 3/12* | (2006.01) | |
| *G01V 11/00* | (2006.01) | |

(52) U.S. Cl.
CPC .............. *G01N 33/18* (2013.01); *G01S 7/025* (2013.01); *G01S 7/411* (2013.01); *G01S 13/885* (2013.01); *G01S 13/904* (2019.05); *G01V 8/005* (2013.01); *G01V 9/02* (2013.01); *G01S 13/867* (2013.01); *G01S 13/9076* (2019.05); *G01S 13/9082* (2019.05); *G01V 3/12* (2013.01); *G01V 11/00* (2013.01); *Y02A 90/30* (2018.01)

(58) Field of Classification Search
CPC ....... G01M 3/183; G01N 22/00; G01V 33/18; G01V 8/005; G01V 9/02
See application file for complete search history.

(56) References Cited

U.S. PATENT DOCUMENTS

| | | | |
|---|---|---|---|
| 4,044,353 A | 8/1977 | Levy | |
| 4,210,023 A | 7/1980 | Sakamoto et al. | |
| 4,381,544 A | 4/1983 | Stamm | |
| 4,744,040 A | 5/1988 | Kawata et al. | |
| 5,321,408 A | 6/1994 | Jean et al. | |
| 5,365,178 A | 11/1994 | Van Der Pol | |
| 5,420,789 A * | 5/1995 | Fulton | G01C 11/025 250/334 |
| 5,557,277 A | 9/1996 | Tricoles et al. | |
| 5,847,567 A | 12/1998 | Kielb et al. | |
| 6,915,689 B2 | 7/2005 | Edvardsson | |
| 7,298,869 B1 | 11/2007 | Abernathy | |
| 7,508,520 B1 | 3/2009 | Lines | |
| 8,096,355 B2 | 1/2012 | McDaniel et al. | |
| 8,106,814 B2 | 1/2012 | Durand et al. | |
| 8,854,253 B2 | 10/2014 | Edvardsson | |
| 9,057,792 B2 | 6/2015 | Abrahamson | |
| 9,285,475 B1 * | 3/2016 | Guy | G01V 9/02 |
| 9,945,942 B2 * | 4/2018 | Guy | G01S 13/885 |
| 2002/0036814 A1 | 3/2002 | Muller et al. | |
| 2004/0099058 A1 | 5/2004 | Edvardsson | |
| 2005/0093548 A1 | 5/2005 | Tricoles | |
| 2007/0024489 A1 | 2/2007 | Cerwin | |
| 2007/0090989 A1 | 4/2007 | Weil | |
| 2009/0024026 A9 | 1/2009 | Simpkin | |
| 2010/0171649 A1 | 7/2010 | Durand et al. | |
| 2012/0262326 A1 | 10/2012 | Abrahamson | |
| 2013/0332115 A1 | 12/2013 | Pratt et al. | |
| 2014/0000348 A1 | 1/2014 | Calvanese Strinati | |
| 2014/0284465 A1 | 9/2014 | Pottorf et al. | |
| 2016/0187524 A1 | 6/2016 | Suhami | |
| 2016/0282463 A1 | 9/2016 | Guy | |
| 2017/0176350 A1 * | 6/2017 | Guy | G01S 7/025 |
| 2018/0224550 A1 | 8/2018 | Lauren | |

FOREIGN PATENT DOCUMENTS

| | | |
|---|---|---|
| CN | 103765246 | 4/2014 |
| CN | 103792586 | 5/2014 |
| CN | 104375202 | 2/2015 |
| EP | 2538192 | 12/2012 |
| JP | S53-111790 | 9/1978 |
| JP | S55-020488 | 2/1980 |
| JP | H06-016844 | 1/1994 |
| JP | H08-005565 | 1/1996 |
| JP | H08-292253 | 11/1996 |
| JP | H08-271642 | 8/2000 |
| JP | 2001-021504 | 1/2001 |
| JP | 2002-315456 | 10/2002 |
| JP | 2003-302465 | 10/2003 |
| JP | 2004-037315 | 2/2004 |
| JP | 2004-037339 | 2/2004 |
| JP | 2005-140607 | 6/2005 |
| JP | 2007-010932 | 1/2007 |
| JP | 2008-164481 | 7/2008 |
| JP | 2010025919 | 2/2010 |
| JP | 2010-236970 | 10/2010 |
| JP | 2011-021912 | 2/2011 |
| JP | 2011-185834 | 9/2011 |
| JP | 2012-079105 | 4/2012 |
| JP | 2014-202690 | 10/2014 |
| RU | 2291344 | 1/2007 |
| WO | WO 01/96818 | 12/2001 |
| WO | WO 2002/023226 | 3/2002 |
| WO | WO 2016/151579 | 9/2016 |

OTHER PUBLICATIONS

Sano et al., "Relation between ERS-1 synthetic aperture radar data and measurements of surface roughness and moisture content of rocky soils in a semiarid rangeland", Water Resources Resrarch, vol. 34, No. 6, pp. 1491-1498, Jun. 1998.

Wang et al., "Estimation of surface soil moisture and roughness from multi-angular ASAR imagery in the Watershed Allied Telemetry Experimental Research (WATER)", Hydrol. Earth Syst. Sci., 15, 1415-1426, 2011.

"Field Estimation of Soil Water Content: A Practical Guide to Methods, Instrumentation and Sensor Technology", Training Course Series 30, Vienna, 2008, IAEA, 141 p.

"Mapping potential shallow groundwater in the Gobi Desert using remote sensing: Lake Ulaan Nuur", Troy Sternberg et al., Journal of Arid Envioronments, vol. 118, pp. 21-27.

Paloscia et al., "A Comparison of Algorithms for Retrieving Soil Moisture from ENVISAT/ASAR Images", IEEE Transactions on Geoscience and Remote Sensing, IEEE Service Center, Piscataway, NJ, US, vol. 46, No. 10, Oct. 1, 2008, pp. 3274-3284.

Salwa Farouk Elbeih, "An Overview of integrated remote sensing and GIS for groundwater mapping in Egypt", Ain Shams Engineering Journal, vol. 6, No. 1, Oct. 8, 2014, pp. 1-15.

Paillou et al., "Mapping of a major paleodrainage system in eastern Libya using orbital imaging radar: the Kufrah River", Earth and Planetary Science Letters, North Holland Publ., CO, NL, vol. 277, No. 3-4, Jan. 30, 2009, pp. 327-333.

Mattia et al., "Hydrology and Earth System Sciences Soil moisture retrieval through a merging of multi-temporal L-band SAR data and hydrologic modelling", Hydrology and Earth System Sciences, vol. 13, Jan. 1, 2009, pp. 343-356.

Mitchell et al., "Towards an operational SAR monitoring system for monitoring environmental flows in the Macquarie Marshes", Wetlands Ecology and Management, Springer Netherlands, Dordrecht, vol. 23, No. 1, Jun. 25, 2014, pp. 61-77.

Walker et al., "High resolution soil moisture mapping", Proceedings of the Fifte Global Workshop on Digital Soil Mapping, Jan. 1, 2012, pp. 45-51.

Francois Jonard, "Soil water content estimation using ground-based active and passive microwave remote sensing: Ground-penetrating radar and radiometer", Unviersite catholique de Louvain, Aug. 2012, pp. 1-195.

(56) References Cited

OTHER PUBLICATIONS

Kentaro Aida and 2 others, Study on Development of a Frequently Applicable SAR Algorithm for Soil Moisture using ALOS/PALSAR, Journal of Japan Society of Civil Engineers, B1 (hydraulic engineering), Japan, Japan Society of Civil Engineers, 2014, vol. 70, No. 4, pp. I_589-I_594.
Japanese Office Action of Japanese Application No. 2017-535094 dated Mar. 3, 2020.

* cited by examiner

SYSTEM AND METHOD OF UNDERGROUND WATER DETECTION

CROSS REFERENCE TO RELATED APPLICATIONS

This application is a continuation-in-part of U.S. patent application Ser. No. 15/014,053, filed on Feb. 3, 2016 which is a continuation in part of U.S. patent application Ser. No. 14/666,648, filed on Mar. 24, 2015, now U.S. Pat. No. 9,285,475, both entitled SYSTEM AND METHOD OF UNDERGROUND WATER DETECTION, and both of which are incorporated by reference herein in their entirety.

FIELD OF THE INVENTION

The present invention relates generally to remote detection of underground liquid. More specifically, the present invention relates to systems and methods for remote detection of underground liquid content using radiofrequency radiation.

BACKGROUND OF THE INVENTION

Shortage in drinking water supply is an acute global problem. Some of this shortage is caused by extensive leakage of drinking water from water supply systems. Water leakage can cause over 20-30% and even over 50% of the losses of drinking water in a typical urban water system. The older the water system the higher the chance for water leakage. Most water leakages occur underground and are hard to detect. Such underground leakages are detected only after causing above the ground floods or massive damage to buildings, infrastructure and the like.

There is no good current solution for detecting underground water leakages. An inspector can use a primitive device placing it above a place where he suspects an underground leakage exists, and attempting to identify water leakage sounds. Another way is to conduct a local excavation at the suspected area. However, local excavations are expensive, and require the use of long algorithms which require pre-obtained data from the area of inspection and from the local authorities (such as municipalities).

SUMMARY OF THE INVENTION

Embodiments of the invention are directed to a system and a method of determining underground liquid content (e.g., drinking water, sewage water, etc.) Embodiments may include: receiving a first scan of an area at a first polarization, the first scan including first radio frequency (e.g., L band microwave) reflections from the area, receiving a second scan of the area at a second polarization, the second scan including second radio frequency (e.g., L band microwave) reflections from the area, the first and second scans being from a first sensor for detecting radio frequency (e.g., L band microwave) radiation reflections attached to an object located at least 50 meters ("m"), 70 m, 100 m or more, above the area and filtering electromagnetic noise from the first scan using the second scan. Embodiments of the method may include creating a water roughness map based on typical water surface roughness values of various types of water sources and the filtered first scan, identifying a first type of water source using the water roughness map and the filtered first scan, and calculating the water content at locations in the area based on the identified first type of water source.

Embodiments of the invention include a method of determining underground liquid content (e.g., drinking water, sewage water, etc.) Embodiments of the method include: receiving a first scan of an area at a first polarization, the first scan including first radio frequency (e.g., L band microwave) reflections from the area, the first scan being from a first sensor for detecting radio frequency (e.g., L band microwave) radiation reflections, the first sensor attached to an object located at least 50 meters ("m"), 70 m, 100 m or more, above the area. Embodiments of the method may further include receiving additional data (e.g., optical data of or representing at least a portion of the scanned area). According to some embodiments, the optical data may be captured at a wavelength in a range between 1 millimeter to 10 nanometers (e.g., from infrared to ultraviolet). According to some embodiments of the method, electromagnetic noise from the first scan may be filtered using the additional (e.g., optical data). Embodiments of the method may include creating a water roughness map based on typical roughness values of various types of water sources and the filtered first scan, identifying a first type of water sources using the water roughness map and the filtered first scan and calculating the water content at locations in the area based on the identified first type of water sources.

Embodiments of the invention may include a method of determining underground polar liquid content (e.g., drinking water, sewage water, etc.). Embodiments of the method may include: receiving, from a radiofrequency (RF) radiation sensor, a main scan of an area, the main scan including reflections from the area at radiofrequency range, the RF radiation sensor being attached to an object located at least 50 meters above the area, and receiving typical roughness values of one or more types of water containing sources or other polar liquids containing sources; filtering from the main scan one or more RF reflections associated with undesired polar liquid types (e.g., drinking water, sewage water, etc.) according to their typical roughness values, identifying a desired type of polar liquid source (e.g., drinking water, sewage water, etc.) in the filtered main scan and receiving from the radiofrequency radiation sensor a set of scans of the area, each scan of the area comprising reflections at the radiofrequency range taken prior to receiving the main scan. In some embodiments, the method may further include calculating the underground polar liquid content (e.g., drinking water, sewage water, etc.) at locations in the area based on the identified first type of polar liquid source (e.g., drinking water, sewage water, etc.) and the received set of scans.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
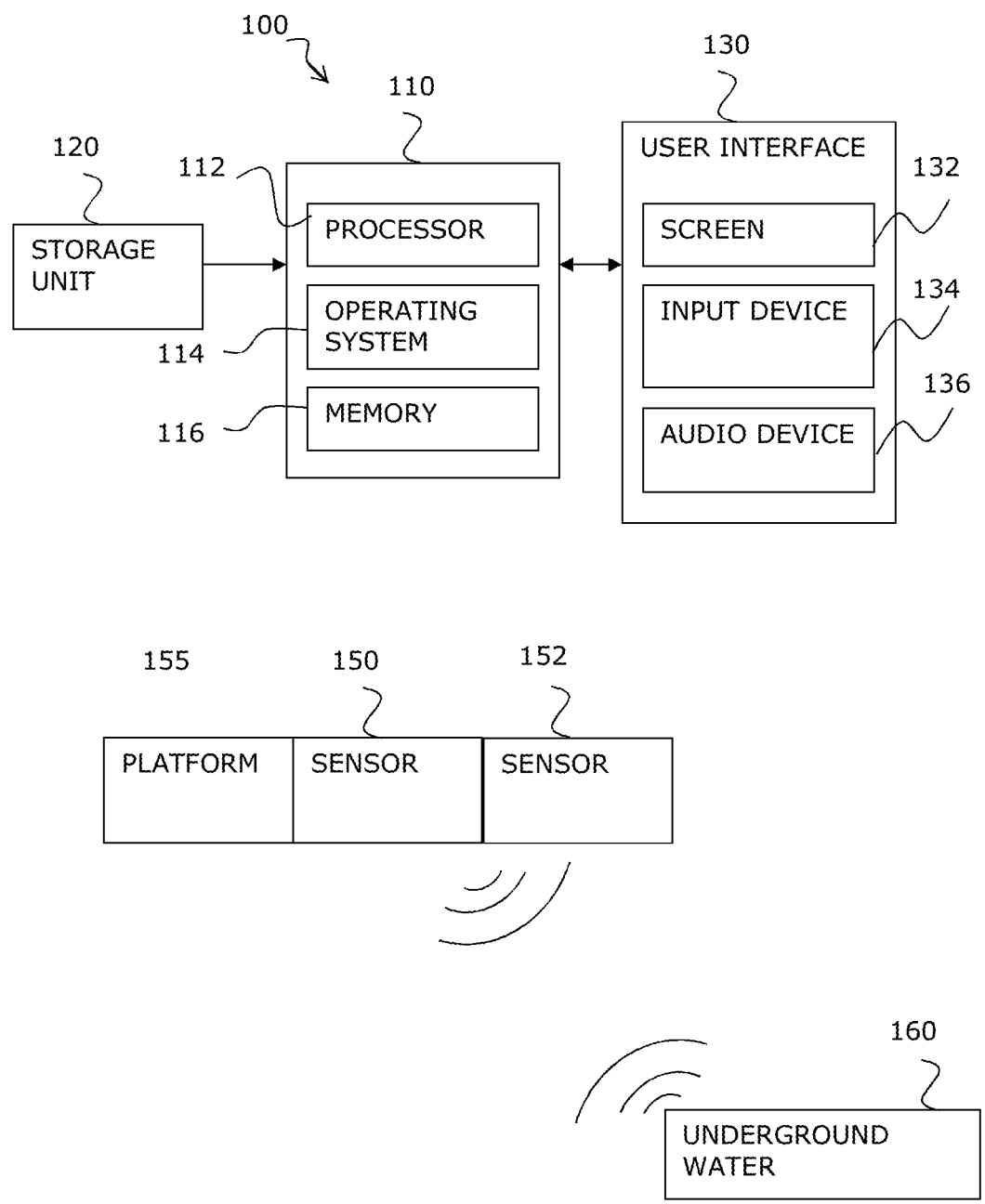
FIG. 1 is high level block diagram of a system for detecting underground water according to some embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other non-transitory processor-readable storage medium that may store instructions, which when executed by the processor, cause the processor to perform operations and/or processes as discussed herein. The terms "plurality" or "a plurality" may be used throughout the specification to describe two or more components, devices, elements, units, parameters, or the like. The term "set" when used herein may include one or more items. Unless explicitly stated, the method embodiments described herein are not constrained to a particular order or sequence of steps. Additionally, some of the described method embodiments, or elements thereof, may occur or be performed simultaneously, at the same point in time, or concurrently.

Embodiments of the invention are related to a method and a system for remote detection of underground polar liquid (e.g., drinking water, sewage water, etc.), for example, drinking water leakage from an urban water system. As defined herein, polar liquids may include any liquid that has molecules with large dipole moments due to bonds between atoms with very different electronegativities. Polar liquids may include, for example, water, sulphuric acid, chloric acid, ammonia, ethanol, and the like. The polar liquid may include small amount of solids, for example sewage water. Water sources such as water pipes, lakes, swimming pools or the like or other polar liquid sources reflect electromagnetic (EM) waves, both underground and above ground level. Water sources or other polar liquid sources may reflect back EM waves at frequencies in the RF range, for example, microwaves in L band frequencies, P band frequencies, C band frequencies and the like. As used herein frequencies in the RF range may include any of the EM wave frequencies that are in the range from 20 KHz to 300 GHz.

As known in the art, every polar liquid source (e.g., drinking water, sewage water, etc.) has typical reflections and typical EM behavior. The type of the polar liquid source (e.g., drinking water, sewage water, etc.) may be identified using these typical reflections. EM sensors placed on an elevated platform for example, a satellite, an aircraft, an air balloon, or the like, may send EM waves at a known frequency (e.g., 1.3 GHz) towards an area and read the EM waves reflected back from that area. The sensor may send a scan that includes all the reflections detected from a particular area to further be processed by a system according to some embodiments of the invention. The sensor may include Synthetic-Aperture Radar (SAR), which uses a motion of a SAR antenna over a target region to provide finer spatial resolution than is possible with conventional beam-scanning radars. The scan may include all the EM reflections received from the area. These reflections may include both reflections from polar liquid sources (e.g., drinking water, sewage water, etc.) and undesired reflections from other bodies in the area, such as buildings, vegetation and other topographical feature of the area. In order to identify the polar liquid-related reflections, the undesired reflections (e.g., EM noise reflection) may be filtered or removed from the scan. In order to reduce (e.g., remove or filter) the EM noise, two or more scans may be taken from the area at two different polarizations, for example, a horizontal-vertical (HV) scan and horizontal-horizontal (HH) scan. The HH reflections may be received from transmitting waves having a horizontal polarization that were received at horizontal modulation. The HV reflections may be received from transmitting waves having a horizontal polarization that were received at vertical modulation.

Some embodiments of the invention may transmit and receive reflections having two different resolutions. For example, HH and HV scans may be received from a first sensor having a first resolution and an additional HH (and/or HV) scan may be received from a second sensor, such that the second sensor has a higher resolution (e.g., 6 m$^3$) than the resolution of the first sensor (e.g., 12 m$^3$). The scans from the first sensor may be used to identify the EM noise reflections and to filter them from (e.g., remove them from) the scan received from the second sensor. In some embodiments, all the scans may be received from a single sensor having a high resolution (e.g., 6 m$^3$, 3 m$^3$). Two HH and HV scans may be received from a single sensor and may include all the information required for filtering (e.g., reducing) the EM noise and receiving a scan having a sufficient resolution. In some embodiments, additional scans having additional polarizations may be received from the single sensor all in the same resolution. Such additional scans may allow further reduction of the EM noise.

After the filtering the EM noise, at least some of the scanned reflections may be identified as polar liquid reflections (e.g., drinking water, sewage water, etc.). Since different polar liquid sources (e.g., drinking water, sewage, seas, lakes swimming pools, etc.) have different typical EM roughness values (typical EM reflections from the surface of the water), it may be possible to distinguish one from the other. In some embodiments, EM roughness values (e.g., surface water roughness values) from sewage pipes, seas, lakes and swimming pools may be filtered or removed from the filtered noise scan thus leaving in the scan only reflection received from polar liquid (e.g., drinking water, sewage water, etc.) leakages. Since the resolution (e.g., at least 3 m$^3$) of the scan is larger than the diameter of the pipes only a leakage larger than this resolution may be detected and not the pipes themselves.

In some embodiments, a drinking water content or amount may be calculated from the drinking water related reflections and converted into quantities of water capacity (e.g., cubic meters/hour, gallons/hour, etc.). This information may be displayed on a geographical map (e.g., a street map of a city) showing, for example, the amount and location of each suspected leakage in a city.

Reference is now made to FIG. 1 which is a high level block diagram of an exemplary system for remote detection of underground polar liquid according to some embodiments of the invention. A system 100 may include a computer processing device 110, a storage unit 120 and a user interface 130. System 100 may receive from a sensor 150 scans that may include reflections in the RF range (e.g., L band, P band, C band microwave reflections and the like) from an area that includes at least one underground polar liquid (e.g., drinking water, sewage water, etc.) source 160. Processing unit 110 may include a processor 112 that may be, for example, a central processing unit (CPU), a chip or any suitable computing or computational device, an operating system 114 and a memory 116. System 100 may be included in a desktop computer, laptop commuter, a tablet, a mainframe computer or the like. Processor 112 or other processors may be configured to carry out methods according to embodiments of the present invention by for example executing instructions stored in a memory such as memory 116. In some embodiments, system 100 may further receive from a second sensor 152 scans having EM reflections in the RF range from an area that includes at least one underground polar liquid source 160.

Operating system 114 may be or may include any code segment designed and/or configured to perform tasks involving coordination, scheduling, arbitrating, supervising, controlling or otherwise managing operation of processing device 110, for example, scheduling execution of programs. Operating system 114 may be a commercial operating system. Memory 116 may be or may include, for example, a Random Access Memory (RAM), a read only memory (ROM), a Dynamic RAM (DRAM), a Synchronous DRAM (SD-RAM), a double data rate (DDR) memory chip, a Flash memory, a volatile memory, a non-volatile memory, a cache memory, a buffer, a short term memory unit, a long term memory unit, or other suitable memory units or storage units. Memory 116 may be or may include a plurality of, possibly different memory units.

Memory 116 may store any executable code, e.g., an application, a program, a process, operations, task or script. The executable code may when executed by a processor cause the processor to detect underground polar liquid and perform methods according to embodiments of the present invention. The executable code may be executed by processor 112 possibly under control of operating system 114. Memory 116 may store data such as for example images, gray scale or intensity levels, scans, reflections, etc.

Storage 120 may be or may include, for example, a hard disk drive, a floppy disk drive, a Compact Disk (CD) drive, a CD-Recordable (CD-R) drive, a universal serial bus (USB) device or other suitable removable and/or fixed storage unit. Content may be stored in storage 120 and may be loaded from storage 120 into memory 116 where it may be processed by processor 112. For example, storage 120 may include scans that may include reflections in the RF range (e.g., L band, P band, C band microwave reflections and the like) of areas at various polarizations received from sensor 150, geographical data related to the scanned area (e.g., a type of soil, amount of humidity in the solid, a road map, etc.), and roughness values of various types of polar liquid (e.g., drinking water, sewage water, etc.) sources or any other required data according to embodiments of the invention.

User interface 130 may be, be displayed on, or may include a screen 132 (e.g., a monitor, a display, a CRT, etc.), an input device 134 and an audio device 136. Input device 134 may be a keyboard, a mouse, a touch screen or a pad or any other suitable device that allows a user to communicate with processor 112. Screen 132 may be any screen suitable for displaying maps and/or scans according to embodiments of the invention. In some embodiments, screen 132 and input device 134 may be included in a single device, for example, a touch screen. It will be recognized that any suitable number of input devices may be included in user interface 130. User interface 130 may include audio device 136 such as one or more speakers, earphones and/or any other suitable audio devices. It will be recognized that any suitable number of output devices may be included in user interface 130. Any applicable input/output (I/O) devices may be connected to processing unit 110. For example, a wired or wireless network interface card (NIC), a modem, printer or facsimile machine, a universal serial bus (USB) device or external hard drive may be included in user interface 130.

Embodiments of the invention may include an article such as a computer or processor non-transitory readable medium, or a computer or processor non-transitory storage medium, such as for example a memory, a disk drive, or a USB flash memory, encoding, including or storing instructions, e.g., computer-executable instructions, which, when executed by a processor or controller, carry out methods disclosed herein.

The storage medium may include, but is not limited to, any type of disk including floppy disks, optical disks, compact disk read-only memories (CD-ROMs), rewritable compact disk (CD-RWs), and magneto-optical disks, semiconductor devices such as read-only memories (ROMs), random access memories (RAMs), such as a dynamic RAM (DRAM), erasable programmable read-only memories (EPROMs), flash memories, electrically erasable programmable read-only memories (EEPROMs), magnetic or optical cards, or any type of media suitable for storing electronic instructions, including programmable storage unit.

A system 100 may include or may be, for example, a personal computer, a desktop computer, a mobile computer, a laptop computer, a notebook computer, a terminal, a workstation, a server computer, a tablet computer, a network device, or any other suitable computing device. Unless explicitly stated, the method embodiments described herein are not constrained to a particular order or sequence. Additionally, some of the described method embodiments or elements thereof can occur or be performed at the same point in time.

Sensor 150 and/or sensor 152 may be any sensor that is configured to scan and detect underground polar liquid, such as underground polar liquid source 160 using electromagnetic radiation. For example, sensor 150 may include a receiver for a radar or Synthetic-Aperture radar (SAR) SAR. Sensors 150 and/or 152 may be placed for example on an elevated platform or structure 155. Elevated platform or structure 155, may be for example, a satellite, an aircraft or an air balloon and may be located at least 50 meters above the ground (i.e., at an elevation of at least 50 m), for example, 70 meters, 100 meters, 150 meters, 500 meters, 1000 meters or more. Sensor 152 may have different detection resolution (e.g., higher resolution) than sensor 150.

Figure 2:
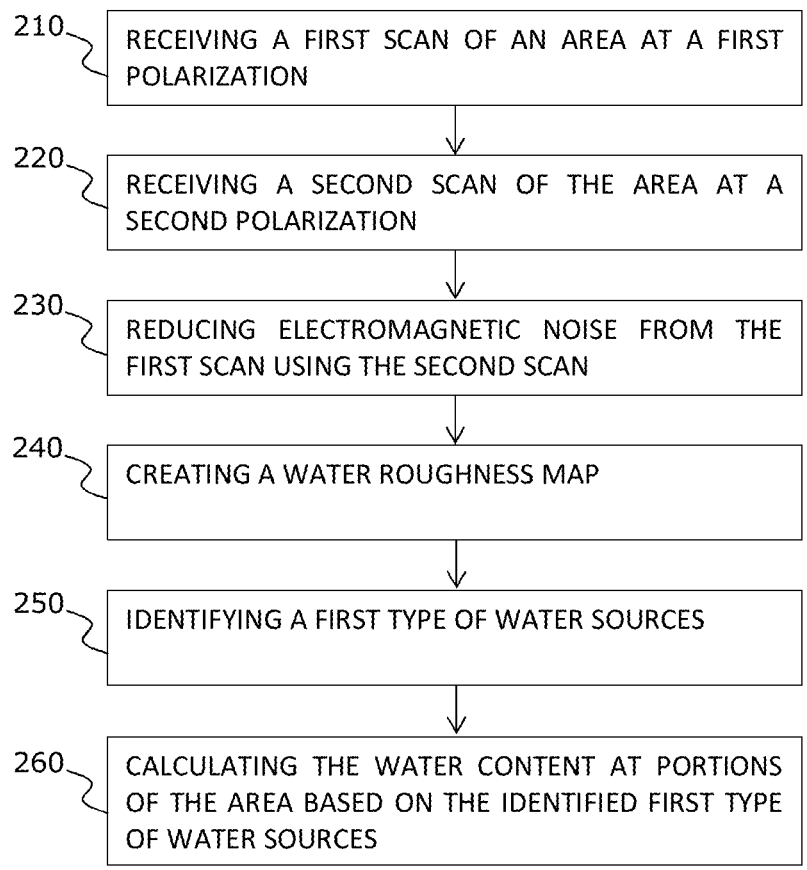
FIG. 2 is a flowchart of a method of detecting underground water according to some embodiments of the invention.

Reference is made to FIG. 2, a flowchart of an exemplary method of remote detection of underground polar liquid according to some embodiments of the invention. Embodiments of the method of FIG. 2 may be performed for example by system 100 or by another system. In operation 210, embodiments of the method may include receiving a first scan of an area at a first polarization. The first scan may be a two-dimensional scan of an area. The first scan may include reflections in the RF range (e.g., L band, P band, C band microwave reflections and the like) from the area. The first scan may include reflections received from a predefined area on the ground, converted into data, e.g., data including pixel data. The size of each pixel may depend on the resolution of a sensor (e.g., sensor 150, 152) located at least 50 meters above the ground. The sensor may receive reflection from both above ground and underground objects. A processor associated with the sensor may convert these reflections into data including pixels having different gray-levels. This data may be received and analyzed by system 100. The size of the area scanned is determined by the sensor (e.g., a SAR sensor) and may be received as raw data. The gray scale level of each pixel converted from microwave reflection of the scan may be related to a reflection intensity level received from a single area unit (e.g., 3 m$^2$) at a respective depth (e.g., 3 m). For example, a pixel may be related to reflections received from 2 m$^3$, 3 m$^3$, 6 m$^3$, 12 m$^3$, or the like.

Reflections in the RF range may be received from a sensor for detecting reflections in the RF range (for example, sensor 150 or 152). The sensor may be attached to an object (e.g., platform 155) located at least 50 m, 100 m, 1000 m or more above the area. A sensor may be attached to an elevated platform, for example, a satellite, an aircraft or an air-balloon. RF waves (e.g., a frequency range of 20 KHz-300 GHz) may be transmitted from a transmitter towards the scanned area and reflected back from the scanned area after interacting with objects both above the ground and underground. The penetration depth of RF waves into the ground may vary with the type of the soil, the amount of moisture in the soil, the structure of the land cover and the like. Exemplary penetration depth may be between soil surface to 3 meters depth from a remote object located at least 50 meters above soil surface. RF waves reflected back from the scanned area may be received and detected by the sensor.

The sensor may identify reflections having different polarizations. Sensors 150 and 152 may each be configured to detect reflections having different resolution, for example, the sensors may be used for receiving scans at resolutions of 6 m$^3$ and 12 m$^3$.

The RF waves may be transmitted in a first polarization, for example, a horizontal polarization or a vertical polarization, and the sensor may detect reflections having various modulations. For example, reflections from waves transmitted at horizontal polarization may be detected at vertical modulation (HV polarization) or may be detected at horizontal modulation (HH polarization). Other polarizations may include vertical-vertical (VV) polarization and vertical-horizontal (VH) polarization.

In operation 220, embodiments of the method may include receiving a second scan of the area at a second polarization. The second scan may include second reflections in the RF range from the same area. In some embodiments, if the first polarization is an HV polarization, than the second polarization may be HH polarization. In some embodiments, the second polarization may be VH polarization or VV polarization. Embodiments of the method may include receiving a third scan of the area at a second polarization (e.g., HH polarization), the third scan including third reflections in the RF range from the area at a higher resolution than that of the first and second scans. For example, if the first and second scans are received from a first sensor, at a resolution of 12 m$^3$, the third scan may be received, from a second sensor for detecting RF radiation reflections, at a resolution of 6 m$^3$. The second sensor may be attached to an object (e.g., a satellite, an airplane or an air-bloom) located at least 50 meters, 100 meters, 1000 meters or more above the area, calibrated similarly to the first sensor, such that a gray level of a pixel converted from an intensity level of microwave reflections in the first and second scans received from a specific location in the area may have corresponding gray level of a pixel (or pixels) converted from an intensity level of microwave reflections in the third scan received from that specific location. For example, if the first and second scans have a resolution of 12 m$^3$ (or 13×6 m$^2$) for every pixel in the first and second scans 4 corresponding pixels (or 2 corresponding pixels) may be received in the third scan. Other numbers of scans may be used.

Figure 3A:
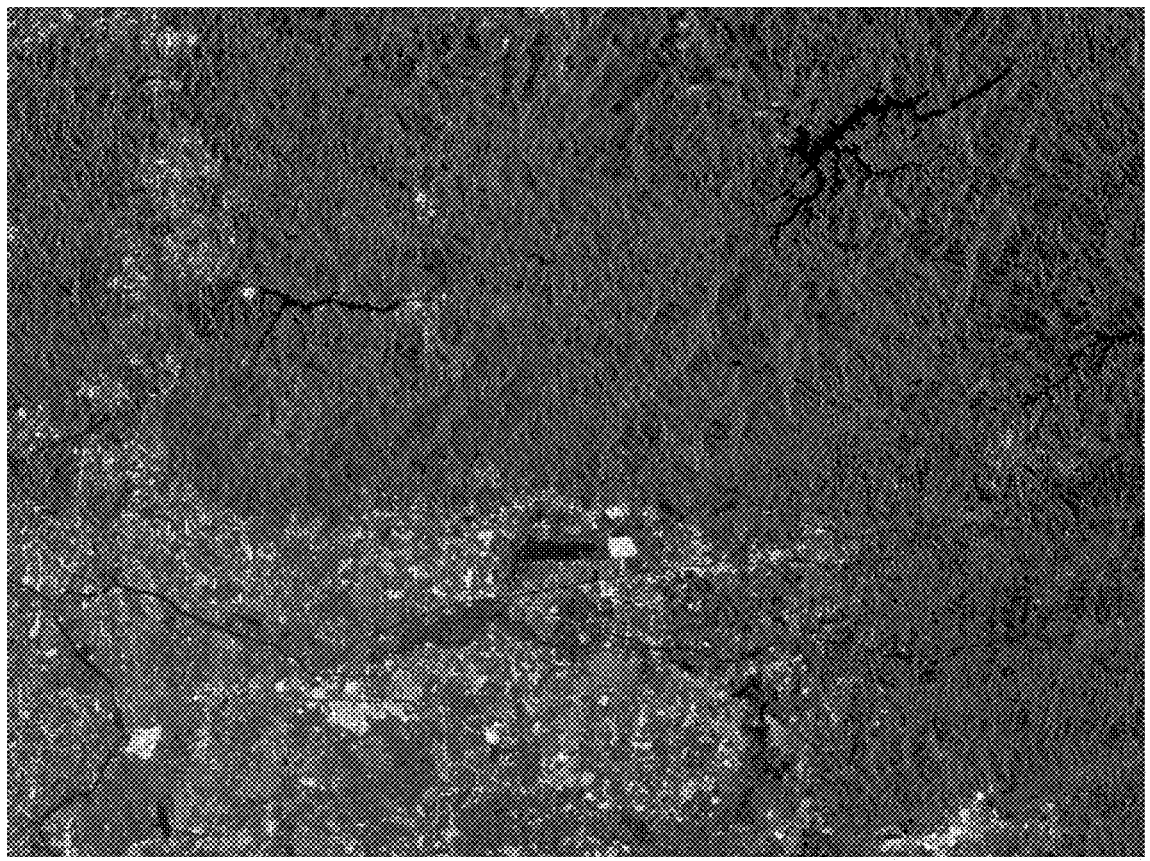
FIGS. 3A-3B are scans of L band microwave reflections from the area a horizontal-vertical (HV) and horizontal-horizontal (HH) polarizations according to some embodiments of the invention.
Figure 3B:
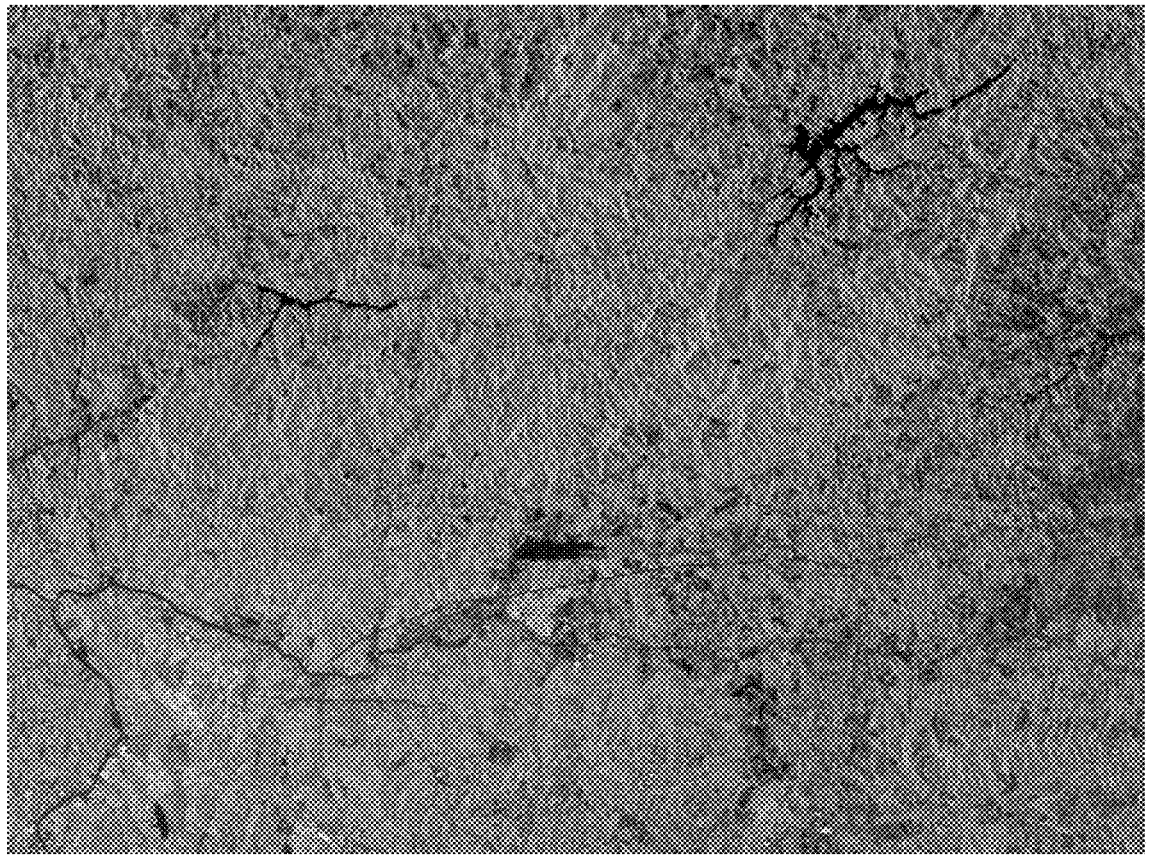

The first, second and optionally the third scans may be received as grayscale images of microwave intensity levels converted into grayscale levels (e.g. each pixel in the map has different gray scale level). Exemplary scans received at a resolution of 12 m$^3$ are given in FIGS. 3A and 3B. FIGS. 3A and 3B are exemplary scans taken above an urban area in Oakland, Calif., as received from an L-band microwave sensor (e.g., a SAR) located on a satellite. FIG. 3A is a scan having a HV polarization and FIG. 3B is a scan having a HH polarization. In some embodiments, the method may include converting the first and second reflections in the RF range from gray scale levels to intensity levels. As used herein gray scale levels may be defined according to the ratio between black pigment or level and white pigment or level at each pixel. The gray levels may be correlated to microwave reflection intensity. The higher the amount of black level or pigment the higher is the intensity of the microwave reflection from a particular area (e.g., pixel). For example, the gray scale level data received from the sensor may be converted to Decibel (dB) intensity level, using for example, equation 1:

$$I_{dB} = 10 \cdot \log(DN^2) - 83 \qquad (1)$$

wherein, $I_{dB}$ is the converted intensity level in each pixel and DN is the gray scale level in each pixel.

It should be understood by those skilled in the art, that equation 1 is given as an example only and converting gray scale levels to other intensity levels using different equations are within the scope of the invention. Embodiments of the method may include converting also the third scan from gray scale into intensity levels.

Embodiments of the method may include receiving a fourth scan of the area at a third polarization, the fourth scan including fourth reflections in the RF range from the area. For example, the fourth scan may include reflections having VH polarization. Embodiments of the method may include receiving a fifth scan of the area at a forth polarization, the fifth scan including fifth reflections in the RF range microwave reflections from the area. For example, the fourth scan may include reflections having VV polarization. The fourth and fifth scans may be received from the first sensor (e.g., a sensor having a resolution of 6 m³).

In some embodiments, all the received scans (e.g., first through the fifth) may be converted from gray scale to intensity levels, using for example, equation (1).

In operation 230, embodiments of the method may include filtering electromagnetic (EM) noise from the first scan using the second scan. The electromagnetic noise may include reflections reflected or bounced from buildings, vegetation or other topographical features located at the scanned area. There are several methods known in the art for filtering EM noise from EM and RF signals and the invention is not limited to a particular method or algorithm. Some exemplary methods for filtering EM noise, from each pixel, according to embodiments of the invention may include reducing noise from buildings using for example the following equations (as with other equations discussed herein, other or different equations may be used):

$$Fd = \frac{1}{2}(HH_{dB}^2 - 2 \cdot HV_{dB}^2) \quad (2)$$

wherein Fd is electromagnetic noise from bouncing reflection from solid objects located in the scanned area, $HH_{dB}$ is the intensity level of HH polarization reflection at that pixel, and $HV_{dB}$ is the intensity level of HV polarization reflection at that pixel. In some embodiments, filtering electromagnetic noise may include filtering reflection received from solid objects located in the scanned area.

$$C = (HH_{dB}^2)/(2Fd) \quad (3)$$

$$Fv = 2 \cdot (\frac{1}{2}HH_{dB}^2 - Fd \cdot C^2) \quad (4)$$

wherein Fv is the calculated electromagnetic reflection noise received from solid objects located in the scanned area.

In some embodiments, reflections from additional polarizations (e.g., VV and VH polarizations) may be used to filter the EM noise. For example, such reflections may be included in an extended equation (2). Various parameters such as Fv and C calculated in equations (2)-(4) may be used to calculate a filtered first scan, according to equation (5).

$$Bs = HH_{dB} - (\text{the EM noise}). \quad (5)$$

wherein Bs is filtered EM noise refection

Figure 4:
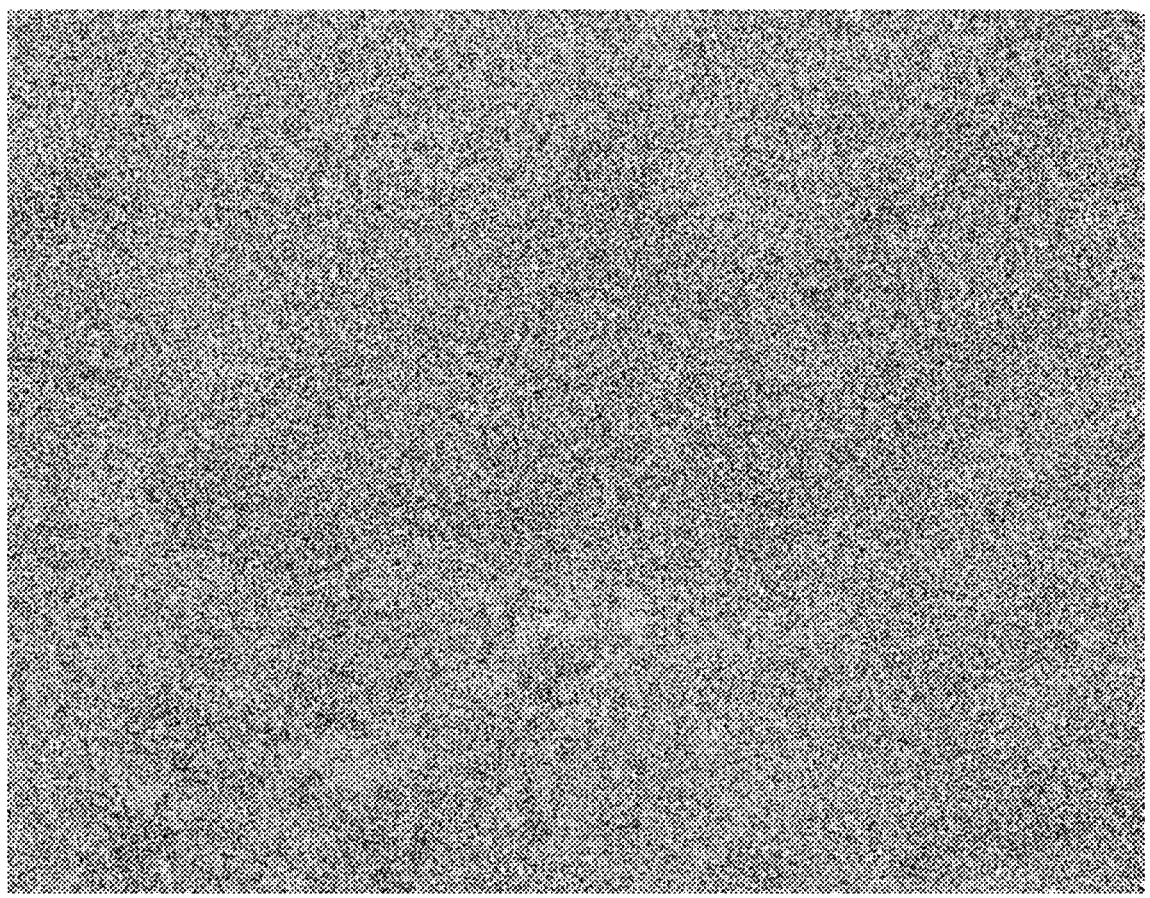
FIG. 4 is the HH polarized scan after filtering electromagnetic noise according to some embodiments of the invention.

An exemplary HH polarized scan (e.g., Bs scan) after filtering electromagnetic noise according to some embodiments of the invention is given in FIG. 4. As one can see in comparison to the scans in FIGS. 3A and 3B, the filtered scan is relatively homogeneous with no large noisy areas or portions. FIGS. 4-7 are gray scale representations of the intensity level at each pixel in the scans. FIGS. 4-7 were created by reconverting the intensity levels used for calculating the various steps of the method from dB to gray scale, using the invert equation of equation (1).

Figure 5:
FIG. 5 is a water roughness map according to some embodiments of the invention.

In operation 240, embodiments of the method may include creating a polar liquid (e.g., drinking water, sewage water, etc.) roughness map based on typical roughness values of various (e.g., a set of) types of polar liquid sources and the filtered first scan. In some embodiments, typical roughness values of various types of polar liquid sources may be stored in a database associated with processor 112, for example, in storage unit 120. Different water sources such as, salty seas, lakes, rivers, swimming pools, sewage pipes and drinking water pipes have different typical reflections recorded and known from the art. This data may be used to create a water roughness map that includes all the undesired water sources, for example, the map may include mapping all reflections related to water sources other than drinking water (e.g., in urban areas sources like rivers, swimming pools and sewage pipes). An exemplary process of creating a water roughness map is given in equation (6).

$$Ks = aBs^2 + bBs + c \quad (6)$$

wherein: a is the average roughness of drinking water, b is the average roughness of open sweet water sources (e.g., swimming pools, fountains and lakes) and c is the average roughness of sewage water. An exemplary water roughness map is given in FIG. 5. FIG. 5 is mostly dark, the dark part is where no water roughness is detected.

In some embodiments, the polar liquid roughness value may be calculated based on the chemical composition of the polar liquid. The amount of chemicals that may be dissolved in the water may affect the dielectric properties of the water. It is well known in the art that the amount of salinity may change the dielectric constant of the water, the higher the salinity the higher the dielectric constant, for a given frequency. Underground polar liquid (e.g., drinking water, sewage water, etc.) having different dielectric constants may have different polar liquid roughness (and different typical microwave reflections) at the same conditions. Some exemplary solutes such as chlorine, calcium and bicarbonates may contribute to the salinity of the water. Drinking water at different areas on the globe has different salinity levels, for example, the amount of calcium in the drinking water in Israel is much higher than the amount of calcium in the drinking water in Germany In Israel the rocks and soil contain large amount of limestone which contributes to the amount of calcium in the water. In some areas there may be a difference in the chemical composition of the water even between two neighboring cities, due to fluorination of the water or other manipulations of the drinking water conducted by, for example, the local municipality.

In some embodiments, when the polar liquid roughness is calculated based on the chemical composition of the polar liquid, for example using equation (6) above, and may include selecting the "a" parameter and/or the "c" parameter of equation (6) based on the chemical composition of the water in the area. In some embodiments, selecting the "a" parameter may include selecting the parameters from a lookup table stored in a memory associated with processor 112, for example, in storage unit 120. The lookup table may include a list of various "a" and/or "c" parameters for water having various chemical compositions. Additionally or alternatively, selecting "a" parameter and/or "c" parameter may include modifying (e.g., by multiplying with a "salinity parameter") the "a" parameter and/or "c" parameter. The salinity parameter may be stored in a memory associated with processor 112, for example, in storage unit 120.

In operation 250, embodiments of the method may include identifying a first type of water sources using the water roughness map and the filtered first scan. Exemplary equations (7) and (8) may be used for calculating value of the first water source.

$$Wc' = Bs \cdot Ks^{Ks} \tag{7}$$

$$Wc = -d \cdot Wc'^2 - e \cdot Wc' - f \tag{8}$$

wherein: Wc is the calculated value of the first water source (e.g., drinking water) in each pixel in the scanned area, d is a constant related to an urban area, e is a constant related to a semi-urban area and f is a constant related to a non-urban area. These constants may vary with the type of polar liquid (e.g., drinking water, sewage water, etc.) source, the type of soil, the amount of moisture in the soil, precipitation (e.g., rain) in the area in a predetermined time interval prior to the calculation (e.g., a week), or the like.

In some embodiments, Wc may be calculated additionally using a correction parameter based on at least one of: the type of the soil in the area, the density of the soil in the area and topography of the scanned area. In some embodiments, calculating Wc may include reducing a moisture level from the identified polar liquid sources received from a database. The moisture level may be calculated based on at least one of: moisture characteristics of a soil in the area and an amount of precipitations (e.g., rain) in the area in a predetermined time interval prior to the calculation (e.g., a week).

Figure 6:
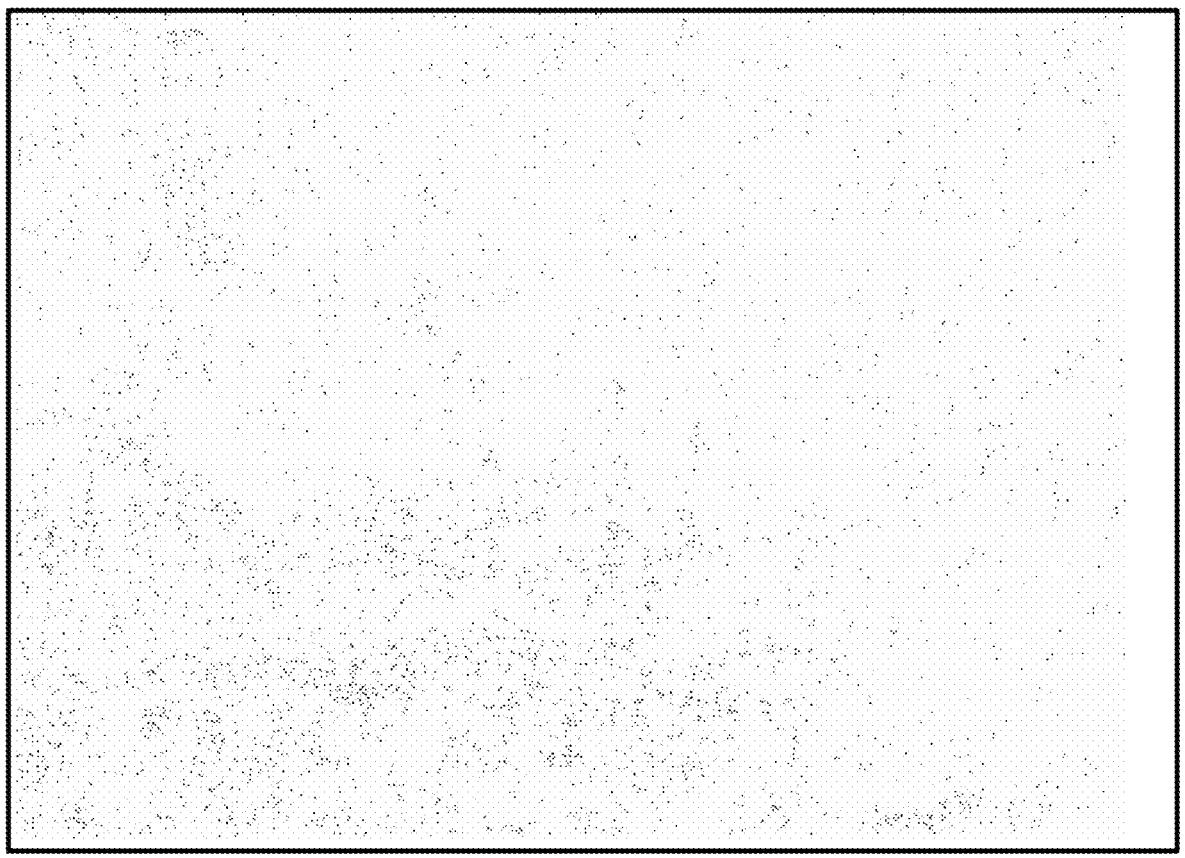
FIG. 6 is a map with identified drinking water sources according to some embodiments of the invention.

FIG. 6 is an exemplary map with identified water sources according to some embodiments of the invention, showing water content in a geographical representation. Since the detection resolution of the drinking water is equal to the resolution of the first, second and optionally third scans, drinking water or other water sources smaller than the scanned resolution (e.g., 3 m², 6 m², 12 m², or the like) cannot be detected.

Figure 7:
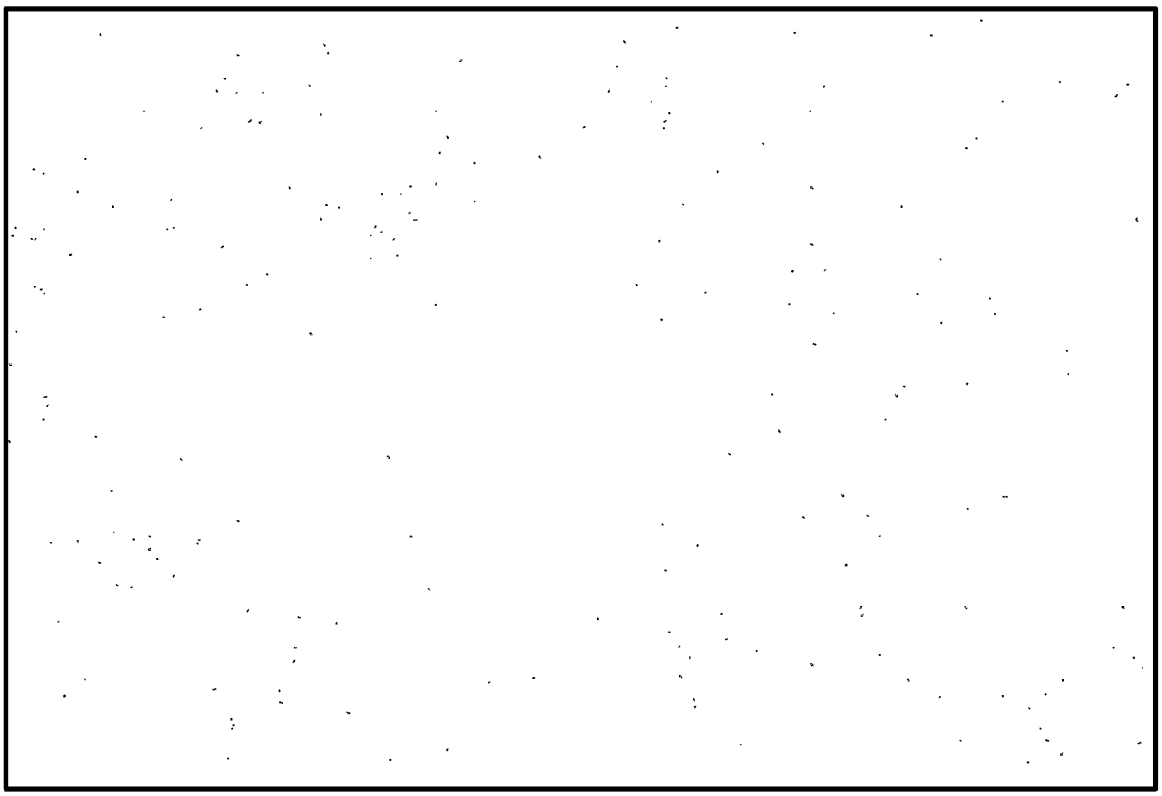
FIG. 7 is a map with identified drinking water leakages according to some embodiments of the invention.

FIG. 7 is an exemplary map with identified drinking water leakages (e.g., a Wc map) according to some embodiments of the invention. Each small dot on the map has different gray scale (e.g., different water content) and corresponds to water leakage. Some water leakages may be larger than areas covered by a single pixel and may include several pixels. Embodiments of the method may include summing or combining together neighboring pixels identified as drinking water leakages to define a single leakage. The intensity levels may be calculated for example in dB values and may be converted to water capacity.

In operation 260, embodiments of the method may include calculating the polar liquid content (e.g., drinking water, sewage water, etc.) at different locations in the area based on the identified first type of polar liquid sources. In some embodiments, since every identified polar liquid source source (e.g., leakage) has its own intensity value, these values may be used to calculate the polar liquid content related to each polar liquid source. The higher the intensity level (e.g., the higher the Wc at that pixel or the sum of Wc in neighboring pixels) the higher is the water content. Embodiments of the method may include converting the calculated water content from reflection intensity levels to quantities of polar liquid capacity for the different area location, for example, in gallons per hour, cubits per hour, etc. The polar liquid capacity may be proportional to the intensity. Different constants may be used to convert the intensity levels to capacities as a function of the capacity unit used (e.g., gallons/hour, cubits/hour, etc.) The calculated intensity level for each pixel may be multiplied by a known constant (e.g., different constants may be used for different capacity units) converting the intensity levels into polar liquid capacities. Some embodiments may include summing capacities calculated for neighboring pixels. Polar liquid (e.g., drinking water, sewage water, etc.) capacities calculated for several neighboring pixels, each corresponding to a location in the scanned area, may indicate that a large underground polar liquid (e.g., drinking water, sewage water, etc.) leakage may be found in the corresponding locations.

Figure 8:
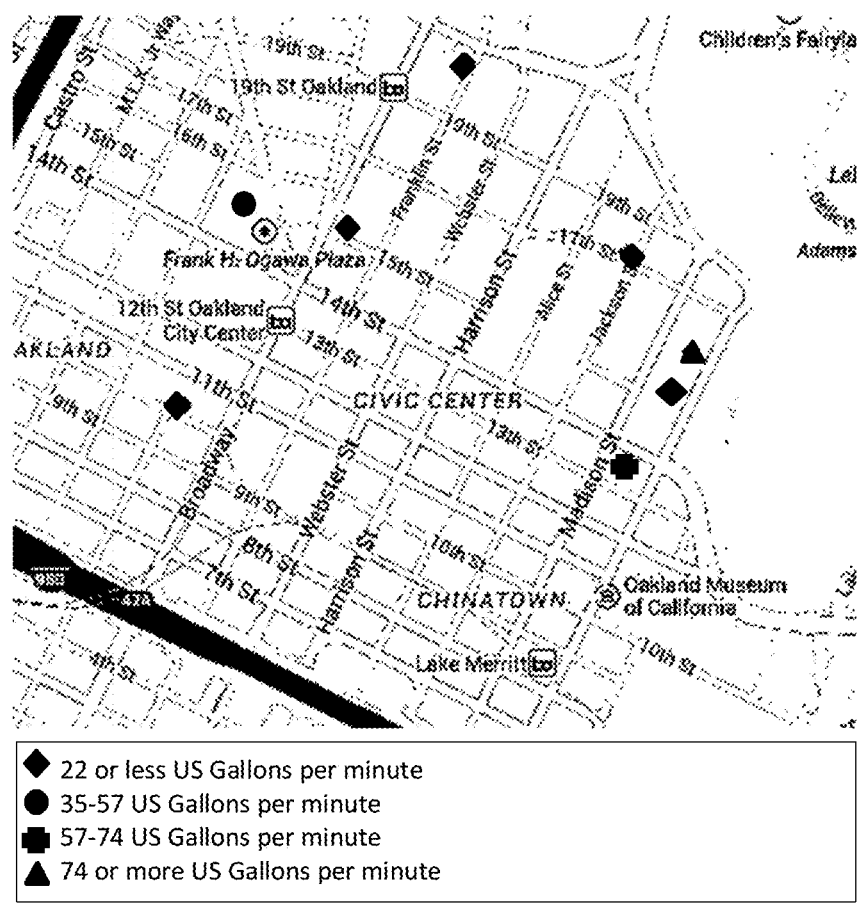
FIG. 8 is a graphical map showing the amount and location of water leakages according to some embodiment of the invention.

Embodiments of the method may include displaying the converted quantities of polar liquid capacity (e.g., drinking water, sewage water, etc.) on a graphical map of the one or more scanned area. The converted quantities may be displayed on: a street map of an urban area, a road map of a county, satellite map, or the like. The converted quantities of polar liquid capacity may be displayed on screen 132 included in user interface 130. An exemplary street map of the Oakland, Calif. city center with locations of drinking polar liquid (e.g., drinking water, sewage water, etc.) leakages is shown in FIG. 8. Since the received scans may include information (e.g., pixels) from a relatively large area, the geographical map presenting the data to a user (e.g., city official) may include only a portion of the scanned area. The user may shift the geographical map on the screen (e.g., using a mouse or a keyboard) covering all areas of interest (e.g., the city quarters) in the scanned area. Some of the detected leakages, illustrated as small gray dots in FIG. 7 were given a polar liquid capacity value and location in the corresponding geographical map (e.g., using coordinates). For example, as illustrated in FIG. 8 each of the marks located in a particular place on the map presents different amounts of polar liquid leakage (e.g. in gallons/hour). It should be appreciated by those skilled in the art that the displayed information may be displayed on top of a Geographic Information System (GIS). It should be further appreciated that additional information may be displayed alongside the polar liquid capacity value and location information, such as, polar liquid pipes, water valves and the like. Such a representation may allow better understanding of the source of a polar liquid leakage and may facilitate decision making in real time.

Figure 9:
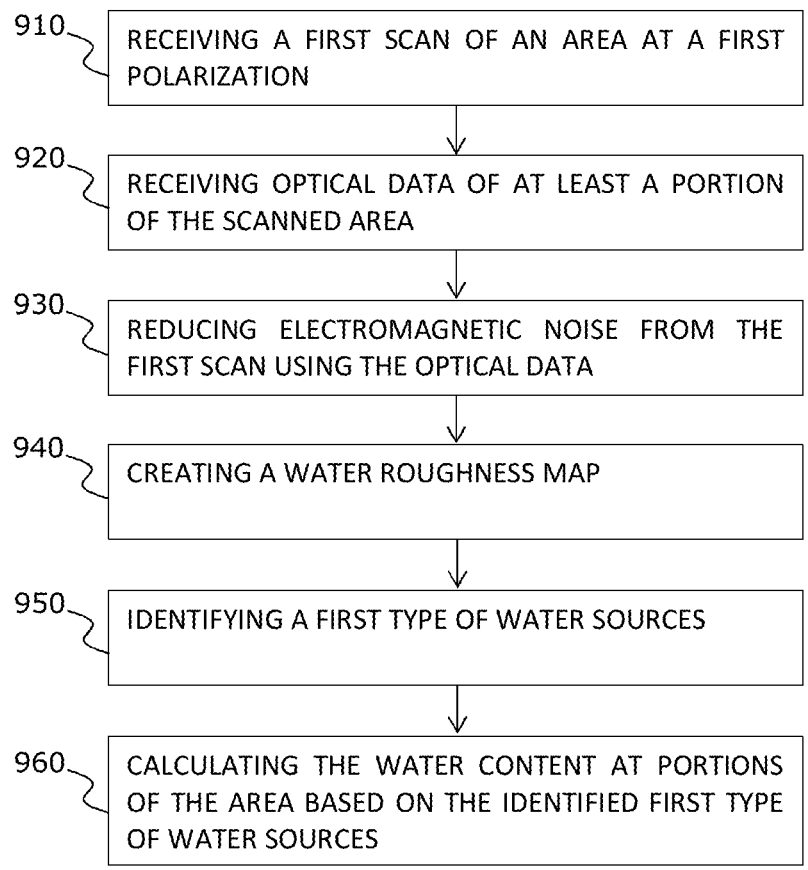
FIG. 9 is a flowchart of a method of detecting underground water according to some embodiments of the invention.

Reference is made to FIG. 9, a flowchart of an exemplary method of remote detecting of underground polar liquid according to some embodiments of the invention. Embodiments of the method may be performed, for example, by system 100 or by another system. In operation 910, embodiments of the method may include receiving a first scan of an area at a first polarization. Operation 910 may be substantially the same as operation 210 of the method illustrated in FIG. 2 and may include the operations, steps and equations described above with respect to operation 210.

In operation 920, embodiments of the method may include receiving optical data of or representing at least a portion of the scanned area. The optical data may be captured in a wavelength in the range of 1 millimeter to 10 nanometers (e.g., from the infrared to the ultraviolet spectrum). The optical data may be received from at least one capturing device or a sensor (such as sensor 150 or 152) located either on platform 155 or elsewhere. The capturing device may include an infrared (IR) camera, a visible light camera and/or an ultraviolet (UV) camera. The optical data may include a satellite optical image, an aerial photograph or the like. Exemplary optical data may include an IR image of the area captured by an IR camera, a visible light photograph of the area (e.g., an aerial photograph) or a UV scan of the area.

In operation 930, embodiments of the method may include filtering electromagnetic noise from the first scan using the optical data. In some embodiments, the method may include comparing the color (e.g., the wavelength) or intensity of neighboring pixels in the optical data to detect differentiations or unexpected colors in the optical data. For example, IR radiation may vary due to temperature differences at various locations in the scanned area. Underground polar liquid in the RF may cool down the temperature of the soil and land being wetted by the underground polar liquid in the RF leakage, in comparison to nearby soil and land. In some embodiments, a detection of an area cooler than nearby areas may indicate the presence of underground polar liquid in the RF. In yet another example, the presence of underground polar liquid (e.g., drinking water, sewage water, etc.) may affect the presence of vegetation at certain areas and/or the color of the vegetation or soil. For example, the presence of underground polar liquid in the RF may cause growth of significant lichen in between paving-stones in a flagging, may cause regeneration of green leaves in some of the vegetation in substantially dry vegetation (e.g., during the summer), may cause a change in the color of the soil (e.g., to become darker) or the like. These changes in the color, if detected, may indicate the presence of underground polar liquid. In some embodiments, the detected indication to a presence of underground polar liquid may be used to filter the EM noise from the first scan.

Some embodiments may include receiving a second scan of the area at a second polarization, the second scan including second reflections in the RF range from the area, the second scan being from the first sensor as discussed with respect to operation 220 of the embodiment illustrated in FIG. 2. In some embodiments, filtering the EM noise from the first scan may further include using the second scan, as discussed with respect to operation 230 of the embodiments of FIG. 2.

Operations 940-960 may be substantially the same as operations 240-260 of the embodiments of FIG. 2 and may include the steps, operations and equations of operations 240-260. The embodiment of FIG. 9 may include any operation or step that may be included and disclosed with respect to the embodiment of FIG. 2.

Figure 10:
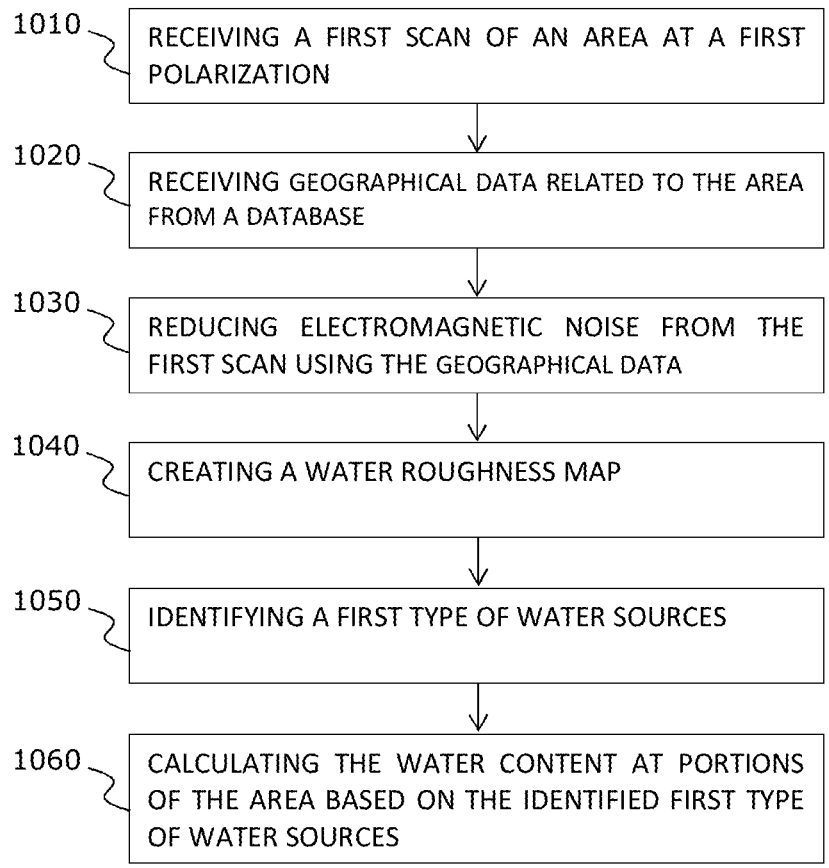
FIG. 10 is a flowchart of a method of detecting underground water according to some embodiments of the invention.

Reference is made to FIG. 10, a flowchart of an exemplary method of remote detecting underground polar liquid (e.g., drinking water, sewage water, etc.) according to some embodiments of the invention. Embodiments of the method of FIG. 10 may be performed for example by system 100 or by another system. In operation 1010, embodiments may include receiving a first scan of an area at a first polarization. Operation 1010 may be substantially the same as operation 210 of the embodiments of FIG. 2 and may include the operations, steps and equations disclosed above with respect to operation 210.

Figure 12:
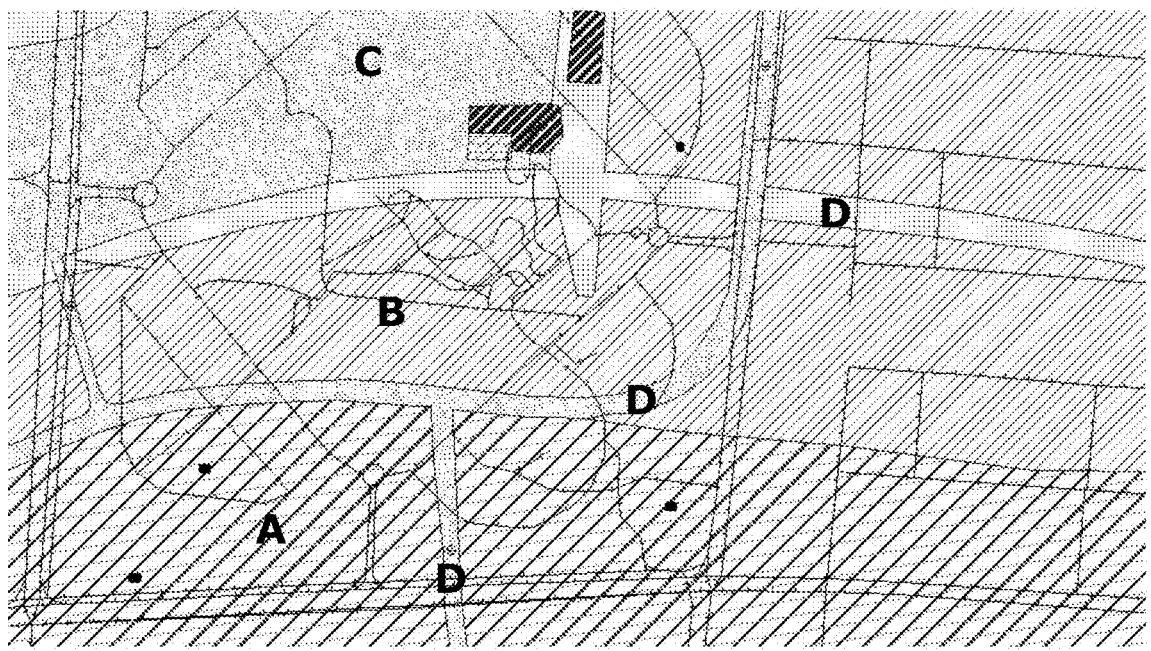
FIG. 12 is a graphical representation of geographical data according to some embodiments of the invention.

In operation 1020, embodiments may include receiving geographical data related to the area from a database. In some embodiments, the geographical data may include a land cover data related to the area. Exemplary land cover may include types such as: a dense urban area, an urban area, a park, an agricultural area, an industrial area, a village and/or paved area. In some embodiments, the land cover data may include classification of various portions in the scanned area into various land cover types, for example, the land cover types listed above. A graphical representation of a scanned area classified to various land cover types is illustrated in FIG. 12. FIG. 12 is a map of a portion of an area presenting 4 land cover types at different location on the map according to one embodiment. The land coves: at location A may be classified as an industrial area, at location B may be classified as urban area, at location C may be classified as a park and at locations D may be classified as paved areas. Other classifications may be used.

In some embodiments, the geographical data may include a location, length, width and height of objects (e.g., buildings) in the scanned area. For at least some of the buildings in the area the location and dimensions of each building may be included in the geographical data.

In operation 1030, embodiments may include filtering electromagnetic noise from the first scan using the geographical data. In some embodiments, filtering the electromagnetic noise may include assigning filtering parameters to each portion of the area based on the land cover type of the classification of the portions of the area. The filtering parameters may be related to the amount of scattering of the microwaves that is typical for each land cover type.

Figure 13:
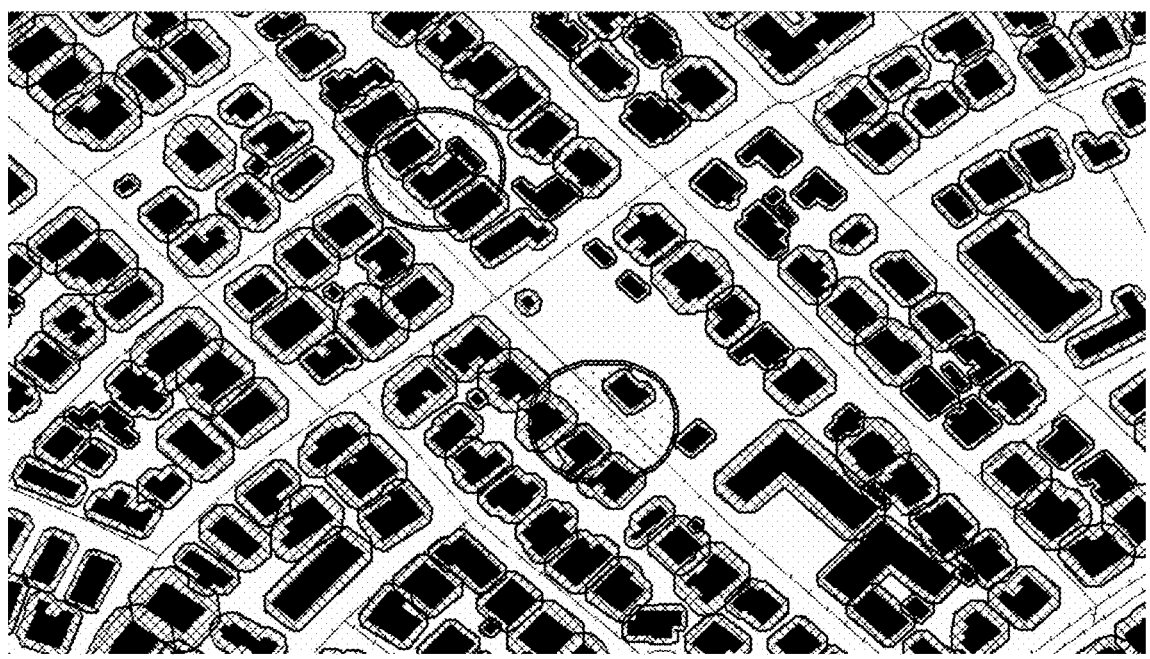
FIG. 13 is a graphical representation of geographical data according to some embodiments of the invention.

In some embodiments, filtering the electromagnetic noise may include calculating the size and location of blind spots areas in proximity to objects in the area, wherein the objects block microwave reflection from the blind spots areas from reaching the sensor. An exemplary calculation of blind spot areas near a building may be done using for example equation (9).

$$S = \tan \alpha \times Hbl \quad (9)$$

Wherein S is the size (in m2) of the blind spot area, a is the off-nadir angle from the satellite to the ground and Hbl is the height of the building. A calculation done for 3 stores building resulted in a blind spot area of 4 m2. FIG. 13 is an illustration of calculated blind spot areas created by nearby buildings according to one embodiment. The squared patterned areas around the dark objects are the blind spot areas. These blind spot areas may be used to filter false readings, for example, if an indication is made that there is a leakage of polar liquid (e.g., drinking water, sewage water, etc.) under an area located in the blind spot area (illustrated as a circle), embodiments may include concluding that these indications are false readings and should be neglected.

Some embodiments may include receiving a second scan of the area at a second polarization, the second scan including second reflections in the RF range from the area, the second scan being from the first sensor as discussed with respect to operation 220 of FIG. 2. In some embodiments, filtering the EM noise from the first scan may further include using the second scan, as discussed with respect to operation 230 of FIG. 2.

Operations 1040-1060 may be substantially the same as operations 240-260 of FIG. 2 and may include the steps, operations and equations of operations 240-260. The embodiment of FIG. 10 may include any operation or step that may be included and disclosed with respect to the embodiments of FIG. 2 and/or FIG. 9.

Figure 11:
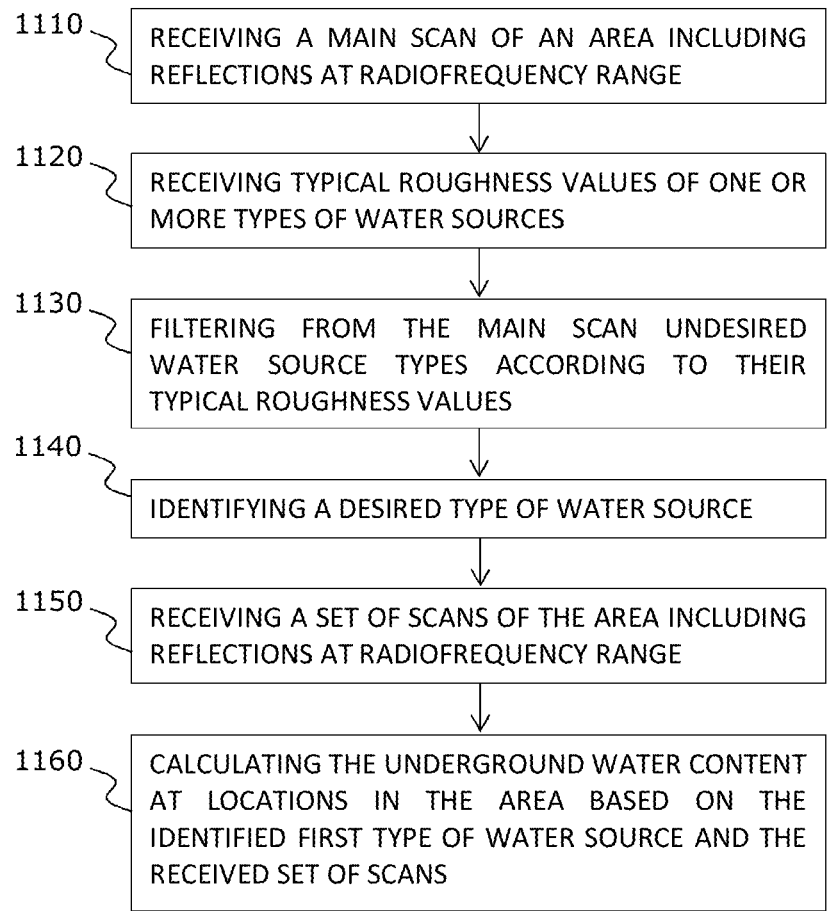
FIG. 11 is a flowchart of a method of detecting underground polar liquid (e.g., water, sewage) according to some embodiments of the invention

Reference is now made to FIG. 11 which is a flowchart of a method of determining underground polar liquid content according to some embodiments of the invention. The method of FIG. 11 may be performed by a processor such as processor 112 of system 100. In operation 1110, embodiments may include receiving, from a radiofrequency radiation sensor (e.g., sensor 150), a main scan of an area. In some embodiments, the main scan may include reflections in the RF range from the area, the sensor being attached to an object located at least 50 meters above the area. In some embodiments, the main scan may be taken at a first polarization, as disclosed herein with respect to operation 210 of the flowchart of FIG. 2.

In some embodiments, at least one other data type may be received, by processor 112. In some embodiments, the additional data may include the following data type: an additional scan (e.g., a second scan) received from the area at a second polarization, the other scan may include second reflections from the area in the RF range, the other scan being from the first sensor, for example, as discussed with respect to operation 220 of the flowchart of FIG. 2, disclosed herein. In some embodiments, the additional data may include a third, fourth and/or fifth scans as disclosed herein. In some embodiments, the additional data may include an optical data as disclosed with respect to operation 920 of the flowchart of FIG. 9. In some embodiments, the additional data may include geographical data as disclosed with respect to operation 1020 of the flowchart of FIG. 10.

In some embodiments, the additional data may allow reduction of electromagnetic noise from the main scan, as disclosed with respect to operations 230, 930 and 1030.

In operation 1120, typical roughness values of one or more types of liquids, such as types of polar liquid sources (e.g., drinking water, sewage water, etc.), may be received by processor 112. In some embodiments, the typical roughness values of various types of liquids such as different types of polar liquid (e.g., drinking water, sewage water, etc.) sources may be stored in a database associated with processor 112, for example, in storage unit 120. Different polar liquid (e.g., drinking water, sewage water, etc.) sources such as, salty seas, lakes, rivers, swimming pools, sewage pipes and treated water and/or drinking water pipes have different typical reflections (i.e., roughness values) recorded and known from the art. In some embodiments, all the reflections related to polar liquid (e.g., drinking water, sewage water, etc.) sources other than the desired one (e.g., underground treated water and underground sewage water and the like) may be identified.

In operation 1130, one or more reflections from undesired polar liquid (e.g., drinking water, sewage water, etc.) source types may be filtered from the main scan according to their typical roughness values. The undesired types of polar liquid (e.g., drinking water, sewage water, etc.) sources may include, for example, salty seas, lakes, rivers, swimming pools, sewage pipes, drinking water pipes and the like. In some embodiments, the typical roughness values may be used to identify the various types of polar liquid (e.g., drinking water, sewage water, etc.) sources and/or to create a polar liquid (e.g., drinking water, sewage water, etc.) roughness map, as discussed with respect to operation 240 of the method of FIG. 2 and equation (6).

In operation 1140, a desired type of polar liquid (e.g., drinking water, sewage water, etc.) source may be identified in the filtered main scan. An example, for such identification is given and discussed herein in operation 250 of the method of FIG. 2.

In operation 1150, a set of scans of the area may be received, by processor 112, from the RF radiation sensor (e.g., sensor 150). In some embodiments, each scan of the area may include reflections in the RF range taken prior to the receiving of the main scan. For example, one or more additional scans may be taken form the area over a predefined period of time, for example, several days, weeks or months. In some embodiments, the scans may be taken at the same polarization as the main scan.

In some embodiments, over the predefined period of time, sensor 150 (e.g., a satellite) may change its location with respect to the area, accordingly, the off-nadir angle at which at least some of the scans were taken may be identified for the at least some scans in the set. As used herein the off-nadir angle is the angle between a direct line connecting the location of sensor 150 and a point in the scanned area and the nadir of sensor 150. The nadir of sensor 150 is the local vertical direction pointing in the direction of the force of gravity at that location of sensor 150. When the nadir is inside the area the off-nadir angle is zero or closed to zero. In some embodiments, at least some of the scans may be modified to correspond to the off-nadir angle at which the main scan was taken. In some embodiments, modifying the at least some scans may include identifying within at least some of the scans at least one anchoring element shown also in the main scan, for example, a main building or any other noticeable landmark. The modifying may further include identifying differences between the at least one anchoring element at at least some of the scans and the main scan, for example, changes in the dimensions, proportions, reflections intensities, etc. of the noticeable landmark. In some embodiments, the identified differences may use to modify other elements in at least some of the scans according to the identified differences.

In some embodiments, the received set of scans may be analyzed to detect changes in the area through time. Such a process is known in the art as interferometry. At least some scans from the received set may be superimposed causing the phenomenon of interference in order to extract information. In some embodiments, using any known interferometry method a first type of changes caused by underground polar liquid (e.g., drinking water, sewage water, etc.) may be identifying in the detected changes. In some embodiments, the detected changes may correspond to ground movements.

In operation 1160, processor 112 may calculate the underground polar liquid content at locations in the area based on the identified first type of polar liquid source and the received set of scans. In some embodiments, the underground polar liquid content may be calculated as disclosed with respect to operation 260 of the method of FIG. 2, operation 960 of the method of FIG. 9 and/or operation 1060 of the method of FIG. 10. In addition to the calculation method disclosed in operation 260, processor 112 may use the received set of scans to increase the accuracy of the size and location of the underground polar liquid content. Processor 112 may use the detected changes that correspond to the ground movements using the interferometry method to refine the underground polar liquid content calculations. For example, the calculation may include calculating the delta between the images.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A method of determining underground polar liquid content, comprising:
    receiving, from a radiofrequency radiation sensor, a main scan of an area, the main scan including reflections at a radiofrequency range from locations in the area, the sensor being attached to an object located at least 50 meters above the area;
    receiving typical roughness values of one or more types of polar liquid sources;
    filtering from the main scan one or more radiofrequency reflections associated with undesired polar liquid source types according to their typical roughness values;

identifying a desired type of polar liquid source in the filtered main scan;
receiving from the radiofrequency radiation sensor a set of scans of the area, each scan of the area comprising reflections at the radiofrequency range taken prior to the receiving of the main scan; and
calculating the underground polar liquid content at the locations in the area based on the identified desired type of polar liquid source and the received set of scans.

2. The method of claim 1, further comprising:
analyzing the received set of scans to detect changes in the area through time; and
identifying in the detected changes a first type of changes caused by underground polar liquid,
and wherein calculating the underground polar liquid content at locations in the area is also based on the identified first type of changes.

3. The method of claim 2, wherein the detected changes correspond to ground movements.

4. The method of claim 2, wherein analyzing the received set of scans comprises:
identifying for at least some scans in the set an off-nadir angle of the sensor at which at least some of the scans scan were taken; and
modifying at least some of the scans to correspond to the off-nadir angle at which the main scan was taken.

5. The method of claim 4, wherein modifying the at least some scans comprising:
identifying within at least some of the scans at least one anchoring element shown also in the main scan;
identifying differences between the at least one anchoring element at at least some of the scans and the main scan; and
modifying other elements in at least some of the scans according to the identified differences.

6. The method of claim 1, wherein the first type of polar liquid source comprises at least one of: underground treated water and underground sewage water.

7. The method of claim 1, further comprising:
receiving additional data; and
filtering electromagnetic noise from the main scan using the additional data.

8. The method of claim 7, wherein the main scan was taken at a first polarization and wherein the additional data comprises at least another scan of the area at a second polarization, the another scan including second reflections from the area in the radiofrequency range, and being from the first sensor.

9. The method of claim 8, further comprising receiving a third scan of the area, the third scan including a third set of radiofrequency reflections from the area at a higher resolution than the resolution of the first and second scans, the third scan being from a second sensor for detecting radiofrequency radiation reflections attached to the object located at least 50 meters above the area.

10. The method of claim 9, further comprising filtering electromagnetic noise from the third scan using at least one of: (i) the main scan (ii) the another scan, and (iii) the additional data.

11. The method of claim 7, wherein filtering electromagnetic noise comprises at least one of:
filtering electromagnetic reflection noise received from solid objects located in the scanned area; and
filtering electromagnetic bouncing reflection noise from solid objects located in the scanned area.

12. The method of claim 7, wherein the additional data comprises optical data of at least a portion of the scanned area, and wherein identifying the first type of polar liquid comprises analyzing the optical data to detect color changes in portions of the area.

13. The method of claim 7, wherein the additional data comprises at least geographical data related to the area received from a database and wherein the geographical data comprises land cover data related to the area, wherein the land cover data related to the area comprises classification of portions of the area into various land cover types, and wherein filtering the electromagnetic noise comprises assigning filtering parameters to each portion of the area based on the classification of the portions of the area to the land cover type.

14. The method of claim 13, wherein the geographical data comprises a location, and dimensions of a solid object in the area, wherein filtering the electromagnetic noise comprises calculating the size and location of a blind spot area in proximity to a solid object in the area, and wherein the solid object blocks radiofrequency reflection from the blind spot areas from reaching the sensor.

15. The method of claim 1, wherein calculating the polar liquid content comprises:
converting the calculated polar liquid content from reflection intensity levels to quantities of polar liquid capacity for the scanned area.

16. A system for determining underground polar liquid content, comprising:
a processor; and
a non-transitory computer readable medium having stored thereon computer-executable instructions which when executed by the processor cause the processor to:
receive, from a radiofrequency radiation sensor, a main scan of an area, the main scan including reflections at a radiofrequency range, from locations in the area the sensor being attached to an object located at least 50 meters above the area;
receive typical roughness values of various types of polar liquid sources;
filter from the main scan one or more undesired polar liquid source types according to their typical roughness values;
identify a desired type of polar liquid source in the filtered main scan;
receive from the radiofrequency radiation sensor a set of scans of the area, each scan comprising reflections at the radiofrequency range taken from the locations in the area prior to the receiving of the main scan; and
calculate the underground polar liquid content at the locations in the area based on the identified desired type of polar liquid sources and the received set of scans.

17. The system of claim 16, wherein the processor further is configured to:
analyze the received set of scans to detect changes in the area through time; and
identify in the detected changes a first type of changes caused by underground polar liquid, and
calculate the underground polar liquid content at locations in the area based on the identified first type of changes.

18. The system of claim 17, wherein the processor further is configured to:
identify for at least some scans in the set an off-nadir angle of the sensor at which the at least some scans scan were taken; and
modify the at least some scans to correspond to the off-nadir angle at which the main scan was taken.

* * * * *